United States Patent
Verboven et al.

(10) Patent No.: US 10,275,870 B2
(45) Date of Patent: Apr. 30, 2019

(54) AUTOMATED SYSTEM AND METHOD FOR CLARITY MEASUREMENTS AND CLARITY GRADING

(71) Applicant: Gemological Institute of America, Inc. (GIA), Carlsbad, CA (US)

(72) Inventors: Marc Verboven, Vloeiende (BE); Troy Blodgett, Flagstaff, AZ (US); Dirk Nuyts, Dr. van de Perrestraat (BE)

(73) Assignee: Gemological Institute of America, Inc. (GIA), Carlsbad, CA (US)

( * ) Notice: Subject to any disclaimer, the term of this patent is extended or adjusted under 35 U.S.C. 154(b) by 0 days.

(21) Appl. No.: 15/918,932

(22) Filed: Mar. 12, 2018

(65) Prior Publication Data
US 2018/0204318 A1 Jul. 19, 2018

Related U.S. Application Data

(63) Continuation of application No. 12/287,186, filed on Oct. 7, 2008, now Pat. No. 9,953,406.

(51) Int. Cl.
*G06T 7/00* (2017.01)
*G01N 21/87* (2006.01)

(52) U.S. Cl.
CPC ............ *G06T 7/0004* (2013.01); *G01N 21/87* (2013.01); *G06T 2207/30108* (2013.01)

(58) Field of Classification Search
CPC .................. G01N 21/87; G06T 7/0004; G06T 2207/30108
See application file for complete search history.

(56) References Cited

U.S. PATENT DOCUMENTS

| | | | | |
|---|---|---|---|---|
| 6,980,283 B1* | 12/2005 | Aggarwal | .............. | G01N 21/87 356/30 |
| 2004/0072137 A1* | 4/2004 | Lapa | ........................ | G09B 5/02 434/386 |
| 2006/0062446 A1* | 3/2006 | Porat | ...................... | G01B 11/24 382/154 |
| 2007/0132983 A1* | 6/2007 | Van de Velde | ........ | G01N 21/87 356/30 |

* cited by examiner

*Primary Examiner* — Kenny A Cese
(74) *Attorney, Agent, or Firm* — DLA Piper LLP (US)

(57) ABSTRACT

A computer-based system and method for taking clarity measurements of a gem, and a computer-readable medium having computer-executable instructions, are provided and include receiving a pixilated image of a gem and identifying pixels representing an inclusion. The method and medium further include determining characteristics of the inclusion as a function of the pixels representing the inclusion, and providing a clarity grade based upon the determined characteristics. Also provided is a method for mapping a gem, and a computer-readable medium having computer-executable instructions, which include receiving a pixilated image of a gem having facet edges, and identifying pixels representing the facet edges. The method and medium further include generating a diagram of the gem, such that the diagram is a function of the pixels representing the facet edges, and superimposing the diagram onto the pixilated image.

22 Claims, 13 Drawing Sheets

Face-Up View

Pavilion View

Side View

AUTOMATED SYSTEM AND METHOD FOR CLARITY MEASUREMENTS AND CLARITY GRADING

CROSS REFERENCE TO RELATED APPLICATIONS

This patent application claims priority from and is related to U.S. application Ser. No. 12/287,186 which was filed on 7 Oct. 2008, which is hereby incorporated by reference in its entirety.

TECHNICAL FIELD

The present invention is directed generally towards analyzing a gem, and more specifically towards utilizing a pixilated image to map a gem and to determine various inclusion characteristics associated with the gem and towards determining a clarity grade from the determined inclusion characteristics.

BACKGROUND OF THE TECHNOLOGY

Today, vision analysis has a growing impact on production, production control, and quality control issues within many industries. The Diamond and Gem industry is no exception, and has adopted digital imaging and vision analysis technology to improve the efficiency of manufacturing processes and improve quality controlling stations. Examples are the high tech computer measuring devices that have taken over the proportion measuring from classic instruments, such as the Gemological Institute of America Proportionscope. Powerful computers and high resolution digital images are now available and have triggered the development of more highly sophisticated vision analysis tools and advanced vision analysis software programs.

The theoretical and practical knowledge in the vision industry is vast, but applying these optical tools and vision analysis knowledge to diamond clarity grading is rather new. There are many considerations in capturing a suitable clarity image, such as lighting and the cost of hardware. Some of these considerations even involve compromises with how else the image can be used. A detailed image of only the grade setting inclusion may be useful for grading clarity, but capturing the whole diamond allows for a broader range of applications, such as placing a more attractive image on a report or capturing symmetry faults. Capturing the whole image is also critical for determining the relative size of the inclusion.

In view of the rapidly growing technological landscape of vision analysis and digital imaging acquisition, developing support tools for clarity grading via vision analysis could be particularly helpful. Such tools, may for example, help to better understand the visual clarity grading decision processes, and also help provide consistency in these processes by providing these tools to grader trainees uniformly. Other methodologies such as x-ray scanning or infrared imaging are inherently limited since they cannot duplicate what a diamond grader sees in the laboratory, whereas vision analysis can replace the human eye with a camera, and a computer application can simulate the decision making processes. The alternative methodologies also are often too costly to consider. Accordingly, there is currently a need for a method and system for analyzing a gem via vision analysis software in support of clarity grading activities.

SUMMARY OF THE INVENTION

This invention addresses the aforementioned problems by providing an improved method and system for analyzing a gem.

In an embodiment of the invention, a method is provided for taking clarity measurements of a gem. The method includes receiving a pixilated image of a gem, designating a region of interest in the pixilated image of the gem which includes an inclusion, analyzing the designated region of interest for pixels that correspond to the inclusion, and determining characteristics of the inclusion as a function of the pixels that correspond to the inclusion.

In a further embodiment of the invention, the analyzing step includes evaluating the designated region of interest using a plurality of vision analysis scripts, wherein each of the plurality of vision analysis scripts include different combinations of pixel analysis algorithms. The different combinations of pixel analysis algorithms in each of the plurality of vision analysis scripts are preferably capable of detecting different types and patterns of inclusions.

In an embodiment of the invention, a method is provided for taking clarity measurements of a gem which includes receiving a pixilated image of a gem, designating a region of interest in the pixilated image of the gem which includes an inclusion, analyzing the designated region of interest for pixels that correspond to the inclusion, and determining characteristics of the inclusion as a function of the pixels that correspond to the inclusion, wherein a precision measurement value of a dimension of the gem is received, a dimension in pixels of the gem is extracted from the pixilated image of the gem, and an image calibration value is generated based upon the precision measurement value and the dimension in pixels. A relative size for the inclusion can be determined as a function of a quantity of pixels representing the inclusion, a quantity of pixels representing the gem, and the image calibration value.

In connection with the embodiments of the present invention, determination of inclusion characteristics may include correlating a plurality of inclusion location identifier regions to areas of the pixilated image of the gem, and identifying an inclusion position for the inclusion as a function of the correlated plurality of inclusion location identifier regions.

In connection with the embodiments of the present invention, determination of inclusion characteristics may include quantifying a brightness of the pixels corresponding to the inclusion, quantifying a brightness of pixels in a designated area adjacent the pixels corresponding to the inclusion, and determining a relief characteristic for the inclusion as a function of the brightness of the pixels corresponding to the inclusion and of the pixels in the designated area.

A still further embodiment of the present invention further includes generating a clarity grade from the determined characteristics of the inclusion.

Still another embodiment of the present invention further includes constructing a gem structure diagram for the gem from the pixilated image of the gem, and combining the gem structure diagram and the pixilated image of the gem, wherein inclusion characteristics of the determining characteristics operation are determined using information from the combined gem structure diagram and pixilated image of the gem.

In another embodiment of the invention, a computer-readable medium is provided having computer-executable instructions thereon for rendering digital content on a device. Included are computer-executable instructions for receiving a pixilated image of a gem; computer-executable instructions for identifying pixels representing an inclusion within a designated region of interest that includes the inclusion, and computer-executable instructions for determining characteristics of the inclusion as a function of the pixels representing the inclusion.

In a further embodiment of the invention, a method for mapping a gem is provided. Within such embodiment, the method includes the steps of receiving a pixilated image of a gem having facet edges, and identifying pixels representing the facet edges. The method also includes the steps of generating a diagram of the gem, such that the diagram is a function of the pixels representing the facet edges, and superimposing the diagram onto the pixilated image. Yet another embodiment of the invention comprises computer-readable media having computer-executable instructions thereon to perform gem mapping operations including receiving a pixilated image of a gem having facet edges, identifying pixels representing the facet edges, generating a diagram of the gem, such that the diagram is a function of the pixels representing the facet edges, and superimposing the diagram onto the pixilated image.

In another embodiment of the invention, a computer based system and method are provided in which a pixilated image of a gem is obtained, facet dimensions are determined from the pixilated image, a region of interest in the pixilated image is designated, scripts are run to isolate inclusions within the designated region of interest, characteristics of the isolated inclusions are determined, and a clarity grade is generated based upon the determined characteristics.

In another embodiment of the invention, a computer-readable medium is provided having computer-executable instructions thereon for rendering digital content on a device. Included are computer-executable instructions for obtaining a pixilated image of the gem from an imaging device, computer-executable instructions for deriving outlines of facet edges and corresponding facet dimensions from the pixilated image, computer-executable instructions for obtaining a designation of a region of interest in the pixilated image, computer-executable instructions for running a plurality of scripts comprising different combinations of vision analysis filters capable of isolating inclusions within the designated region of interest, computer-executable instructions for determining characteristics of inclusions isolated by the plurality of scripts from pixels of the pixilated image corresponding to isolated inclusions, and computer-executable instructions for generating a clarity grade based upon the determined inclusion characteristics.

As will be appreciated upon consideration of the following detailed description of the invention and accompanying drawings, there are many advantages and features of the present invention, which in turn lead to many new and useful applications of the invention.

DETAILED DESCRIPTION OF THE INVENTION

The present invention is directed towards providing an improved method and system for analyzing a gem. More specifically, the present invention provides a method and system for utilizing a pixilated image to map a gem and to determine various inclusion characteristics associated with the gem, and for using of such characteristics to generate a clarity grade. Accordingly, the present invention has special utility in the field of clarity grading. In addition, the present invention is particularly suited for implementation in a computer application.

Figure 1:
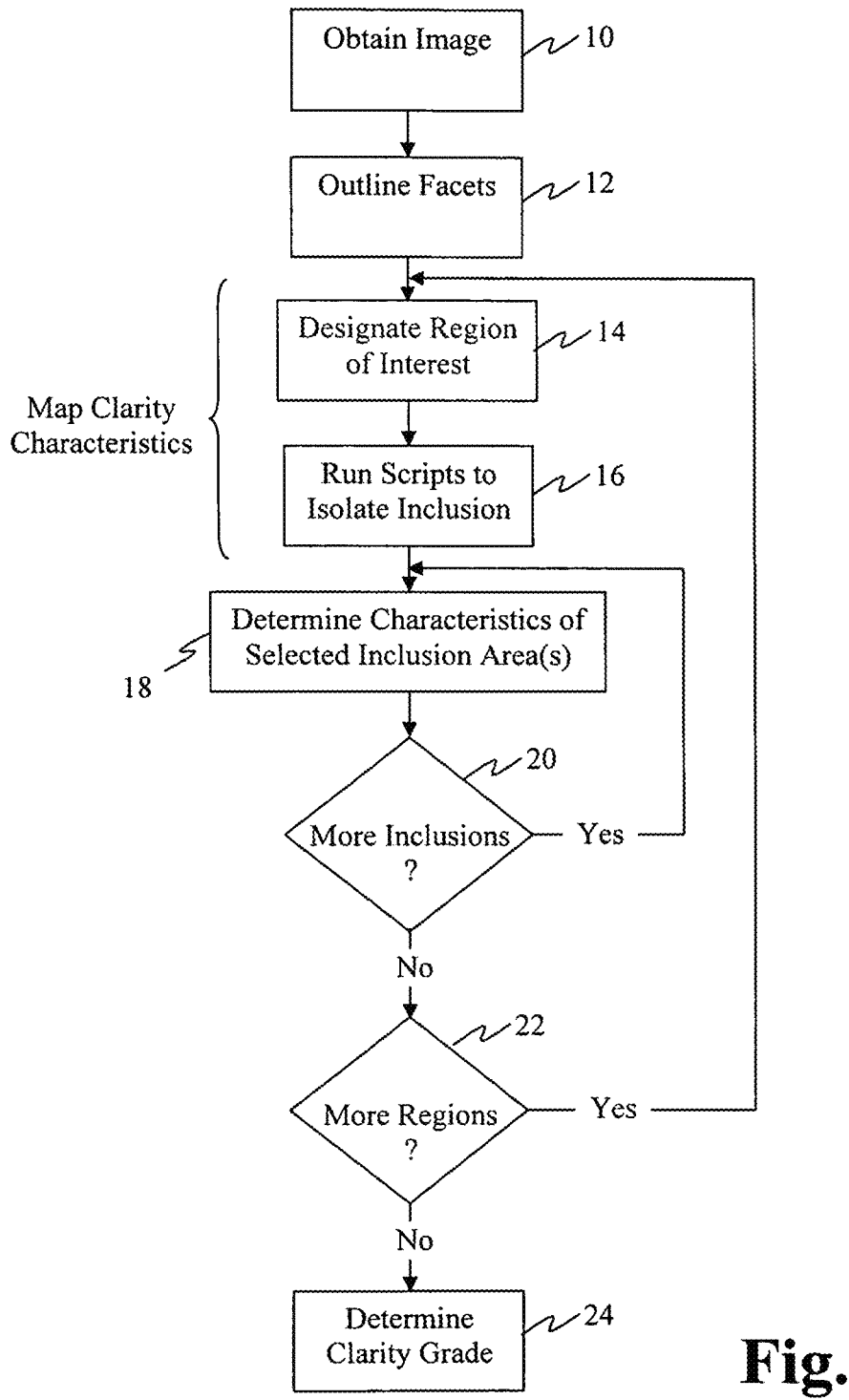
FIG. 1 is a simplified flow diagram of operations involved in determining the clarity grade of a gem in accordance with an embodiment of the invention.

FIG. 1 provides an overview, by way of a simplified flow diagram, of operations involved in determining the clarity grade of a gem in accordance with an embodiment of the invention.

To begin, in operation 10 an image is obtained of the gem to be graded in a form which is or is capable of being pixilated, and a pixilated image is obtained. In operation 12, in an embodiment of the invention, information about the facets of the gem are obtained, and an outline of the facets of the gem may be created, from the pixilated image. Operation 12, will be described in further detail hereafter in connection with FIGS. 3 through 5A-5C.

Preferably, in operation 14, a region of interest ("ROI") is designated by an operator or user. The pixels within the designated ROI are then evaluated for inclusions. Operation 16 involves running analyses called "scripts" on the pixels within the region of interest in order to isolate any inclusions that may be located within the region of interest. These scripts are configured and selected for their ability to isolate typical types and patterns of inclusions in a pixilated image. Alternatively, and/or if needed, manual isolation of inclusions may be undertaken.

Following the isolation of the inclusions, operation 18 determines characteristics of the inclusions which were isolated in operation 16. As will be described in greater detail hereafter, such inclusion characteristics may include type, relative area, number, relief, and location (or position), among other characteristics. Blocks 20 and 22 repeat operations 14, 16 and 18, as needed, to process the inclusions in the gem. In block 20, if there are more inclusions to be characterized in the current region of interest, operation 18 is repeated. If no further inclusions are to be characterized for the current region of interest, block 22 then determines if the are other regions of interest to be evaluated. If so, operation 14 is then accessed to permit the designation of a different region of interest for analysis, and then operations 16 and 18 are repeated as needed.

Once characteristics of the inclusions have been obtained, operation 24 generates a clarity grade for the gem based upon the inclusion characteristics determined in the preceding operations.

A more detailed description will now be provided of the various operations identified in FIG. 1.

Figure 2A:
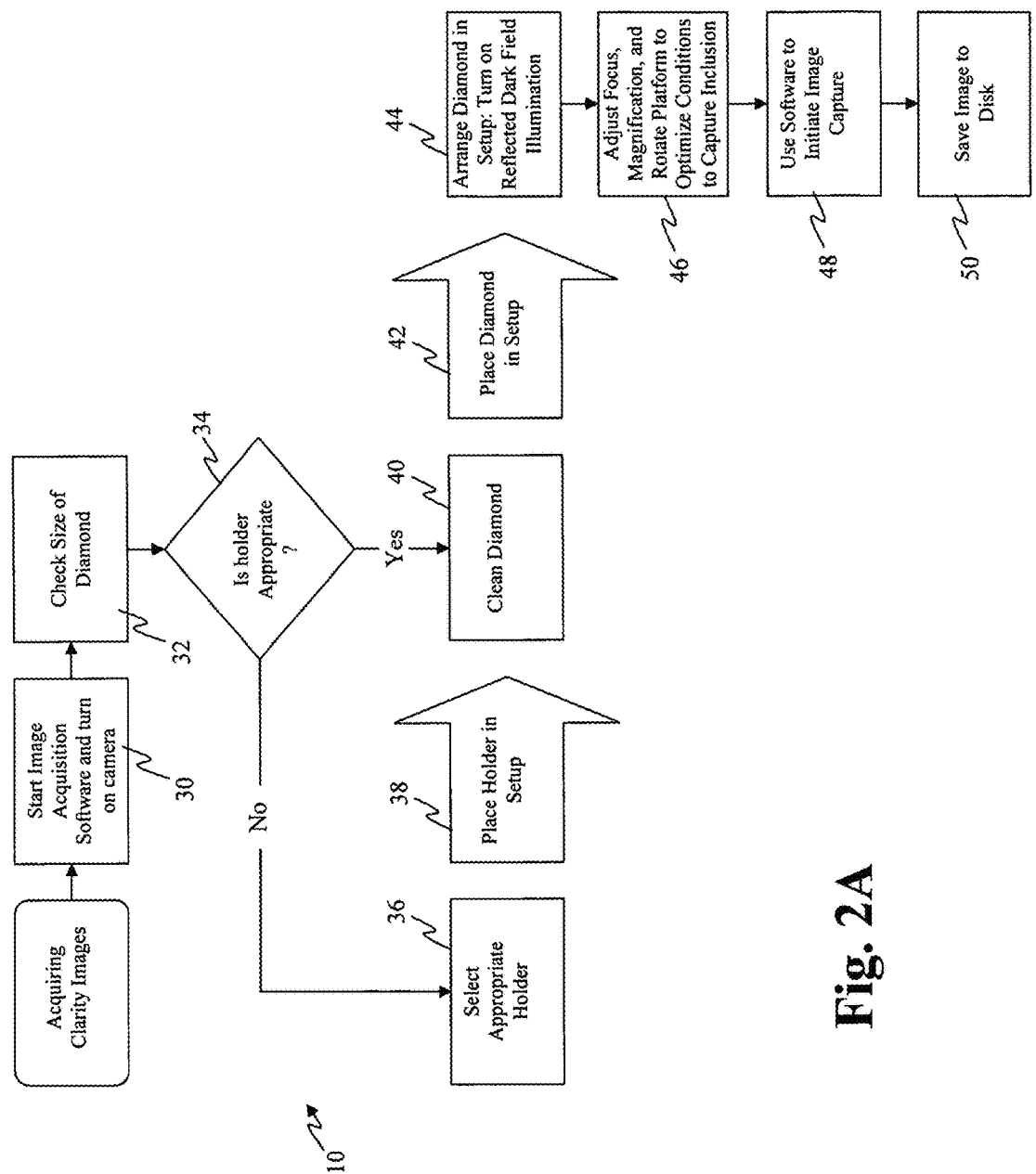
FIG. 2A is a simplified flow diagram of operations involved in obtaining a pixilated image of a gem for purposes of clarity grading in accordance with an embodiment of the invention.

Referring now to FIG. 2A, various steps involved in the obtain image operation 10 of FIG. 1 are depicted. In step 30 the operator starts up image acquisition software, and powers-up the camera, or other imaging device. Software such as the application called Nikon Capture, available from Nikon Corporation of Tokyo, Japan, can be used as the image acquisition software when a still camera is being used. Next, in step 32, a check is made of the size of the gem being imaged. Then it is determined whether the holder currently being used has the appropriate configuration for the gem being imaged. See step 34. If not, a more appropriate holder is selected and installed, steps 36 and 38, respectively. Once an appropriate holder is in place, the gem is cleaned, and placed in the holder. See steps 40 and 42, respectively.

Figure 2B:
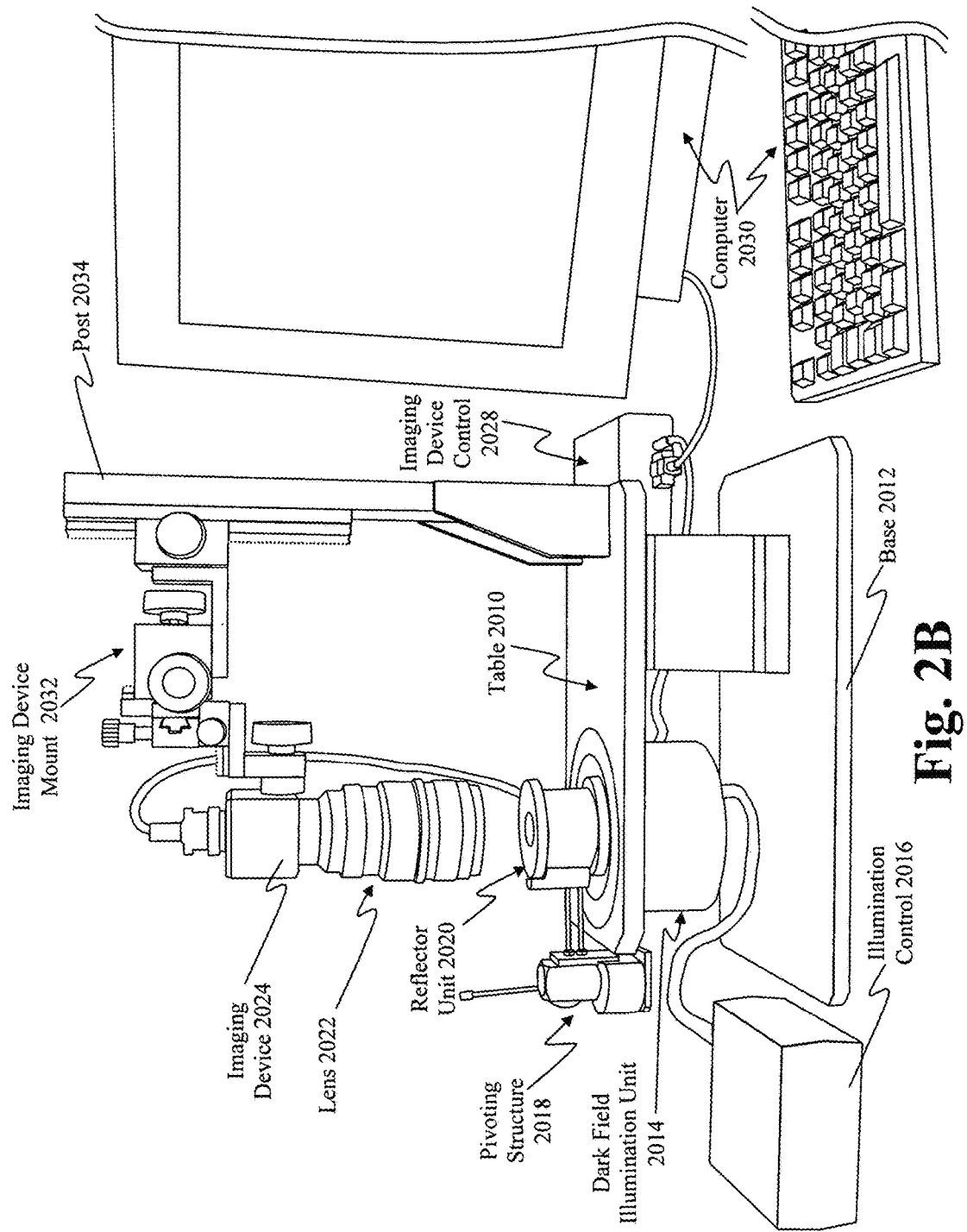
FIG. 2B is a simplified illustration of an embodiment of an image capturing and processing configuration for obtaining a pixilated image of a gem for purposes of clarity grading in accordance with an embodiment of the invention.

The "setup" referred to in FIG. 2A is an apparatus which supports and provides illumination of the gem being analyzed. Preferably the setup is a dark field illumination apparatus that provides reflected dark field illumination, such as that described in co-pending U.S. patent application Ser. No. 12/287,188, now issued as U.S. Pat. No. 8,289,621 entitled "Reflected Dark Field Method and Apparatus," filed even date herewith, and incorporated herein by reference in its entirety. As described in the referenced application, reflected dark field illumination is provided to illuminate the gem being imaged in a manner which minimizes direct (bright) reflections off of crown (or other face-up) facets and provides an increased light intensity level which allows for faster shutter speeds and more ideal exposure settings when imaging gems. FIG. 2B illustrates a configuration of imaging device, lens, table, and stage, and which employs the reflected dark field illumination, for obtaining a pixilated image of a gem for purposes of clarity grading in accordance with an embodiment of the invention. FIG. 2B is described in more detail in the above incorporated by reference application.

Briefly, in FIG. 2B it can be seen that a table 2010 is supported above a base 2012. A dark field illumination unit 2014, as described in the above incorporated by reference application, is coupled to and positioned below table 2010. Illumination control 2016 is provided by which the light sources within dark field illumination unit 2014 are controlled. Included are switches and intensity controls by which the output of various combinations of LEDs within dark field illumination unit 2014 may be activated and/or adjusted. A pivoting structure 2018, as described in the above incorporated by reference application, is coupled to a reflector unit 2020 which is positioned above table 2010. In FIG. 2B, reflector unit 2020 is shown in its down position, in registration with dark field illumination unit 2014. Also shown in FIG. 2B is a lens 2022 and imaging device 2024 supported above and in registration with reflector unit 100. Imaging device 2024 is shown electrically coupled to imaging device control 2028, which communicates with computer 2030. The imaging device 2024 is supported by an imaging device mount 2032, which itself is supported by post 2034. Post 2034, in turn, is coupled to and supported by table 2010. With such a configuration, an operator is able to control the imaging device 2024 to view, capture, and store images of the gem under inspection, and to further process the captured images, such as in a clarity grading operation.

Returning to FIG. 2A, in step 44, the gem is arranged in the setup, and reflected dark field illumination is turned on. Then, in step 46, focus, magnification and position adjustments are made to optimize the conditions for capturing an image of the inclusions in the gem. Historically, the face-up position of a gem has been the main observation direction for visual clarity grading of all clarity grades from VVS2 down. Therefore, the face-up position has been adopted as the preferred observation direction for data collection and for taking digital images in the preferred embodiment of the present invention. Other observation directions, such as those arrived at by tilting, add considerable complexity without offering a clear benefit, so these other observation directions while also possible alternatives for use in clarity grading, are not discussed in detail here.

In step 48, the imaging software is used in conjunction with the imaging device, such as a digital camera, to capture images of the gem. In step 50, the captured images are saved, such as by storing the images on a disk or other media.

Figure 4:
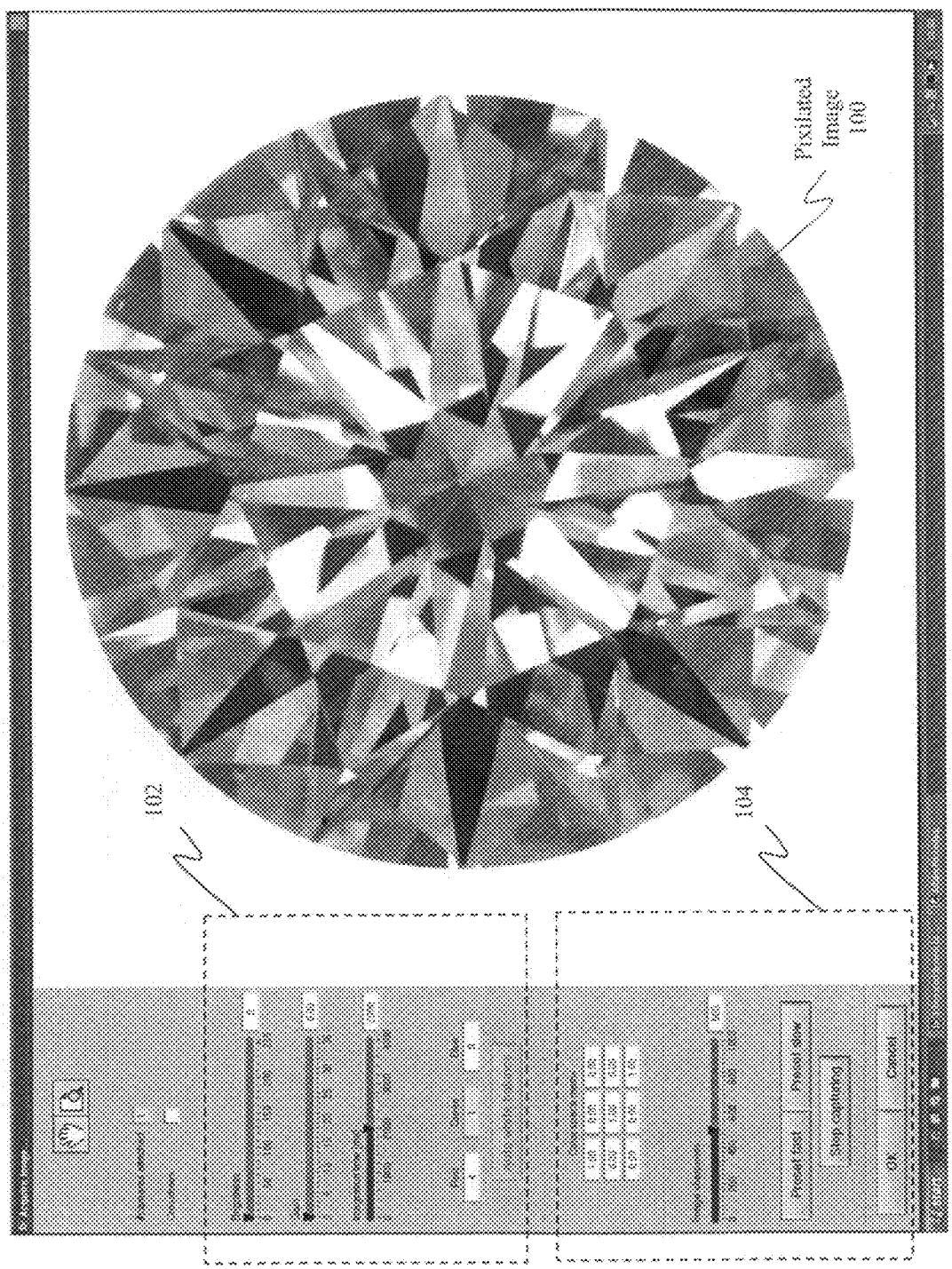
FIG. 4 is an exemplary illustration of a screen configuration employed during the acquisition of a pixilated digital image, and of an acquired pixilated digital image of the type operated upon in embodiments of the present invention.

An exemplary illustration of a pixilated image 100 used in accordance with the invention is provided in the screen shot of the imaging acquisition in FIG. 4. As can be seen in the left hand side of the screen shot, the imaging software provides various controls for the image capture. For example, controls 102 relate to brightness, gain, and integration time. Controls 104 relate to image sharpness as well as provide a color space matrix.

Because the present invention involves extrapolating data from such a pixilated image of a gem, obtaining a high quality digital image is important. As such, a brief discussion of several image-acquisition issues which have been encountered is provided below.

Initially, the first digital images which were experimented with in the development of the invention were created by digitizing traditional slides. Thereafter, a hardware setup, including a Model D1 digital camera by Nikon Corporation, of Tokyo, Japan, was used to provide a means to make digital images of high resolution without any further processing. As a result of the camera's sensor resolution, the generated images had about 6-7 micron pixels, which sets the threshold for clarity analysis of high clarity diamonds. With such a sensor resolution, inclusions smaller than this threshold (such as a high VVS1 pinpoint), cannot be resolved, and even resolvable pinpoints can be difficult to pick out on an image. Further, dust and grease can be mistaken for VVS1 and VVS2 pinpoints and feathers. These are some of the limitations of the technology. However, it is noted that when such a device is used to image a diamond, and no inclusions can be resolved in the acquired image, this would be an indication that the diamond is a high clarity diamond. As imaging devices with sensors of better resolution capabilities become available, it is envisioned that such devices may be utilized to obtain digital images in accordance with the present invention.

The file size of digital images to be stored has also been an issue of concern because of the potential volume of images that need to be captured. To keep the file size as small as possible (without losing information after compression of the original image), a JPEG 2000 standard may be used. Different software plug-ins for this file format exist from different manufacturers (for example, the LEAD Image Builder Photoshop plug-in, from Adobe Corporation, of San Jose, Calif., was employed here). In theory, the JPEG 2000 standard allows for compressing up to 95% without sacrificing pixel information. Alternatively, the more widely used standard JPEG image format may also be employed.

A particular limitation of still photographs is that the proper orientation of the diamond or other gem being imaged can only be checked after the image is shot. A real time camera, however, would acquire images continuously while the diamond is being oriented allowing the process of setting up to take much less time because the image can be checked continuously for better optimization of the image. Therefore, in another embodiment of the invention, a real time camera, and real time camera image acquisition software, may be used as the imaging device, such as that available from RedLake, Inc./IDT of Tallahassee, Fla. For example, the real time camera imaging device may be RedLake Inc./IDT product model MegaPlus ES-4020—color; having 2048×2048 resolution, interline transfer CCD; 7.4 micron square pixels; a well capacity of 40,000e—per pixel; a 60 percent fill factor; a progressive scan; with clear glass filter; F-Mount lens adaptation; and capable of 15 full frames per second. Accompanying the MegaPlus ES-4020 are a camera head controller unit that provides CameraLink and FireWire interfaces, and control software. Preferably, the real time camera is used with a NIKKOR 2.8 60 mm micro lens and NIKON PK 12 extension ring, manufactured by Nikon Corporation of Tokyo, Japan.

Returning to FIG. 1, after obtaining a suitable digital image in operation 10, the facets of the gem are mapped in operation 12. Further details of operation 12 are provided in FIG. 3, which provides a block diagram for mapping a gem according to an embodiment of the invention. As illustrated, the process begins at step 60, wherein a pixilated digital image of a gem is received, for example, the image 100 of FIG. 4. The gem images may be loaded from a designated file directory, for example. Next, pixels representing the facet edges of the gem are identified at step 62. Vision analysis software can be utilized to find all the facet edges of a gem for the surfaces through which the clarity analysis is being conducted, for example all of the facet edges of a face-up diamond. Such software preferably uses edge detection techniques and expected shape and facet distributions to fit a model to the detected edges. Such vision analysis software may be based upon the LabVIEW application in the Vision Builder programming environment of National Instruments Corporation of Austin, Tex. From the identified facet edges of the gem, a modeled outline (also referred to as a gem structure diagram) is then generated in step 64, and superimposed onto the actual digital image in step 66. The combination of actual image and superimposed modeled outline may then be used to measure the diameter and other dimensions (in pixels) of the gem and the area and other dimensions of an inclusion, as well as to locate the position of an inclusion.

Uses of such collected information, in accordance with embodiments of the invention, are discussed in greater detail as a part of the description which follows of the determination of the relative size of inclusions. Briefly, clarity grading typically considers the relative size of an inclusion, for example, the relative area of an inclusion to the area of a face-up gem. Therefore, measurements of the actual size of inclusions are typically not a parameter of critical interest for clarity grading. For example, a small inclusion in a small diamond will tend to have more impact on the clarity than the same inclusion in a larger diamond. In accordance with a preferred embodiment of the invention, in order to calculate the relative size of an inclusion, the area of the inclusion and the area of the face-up diamond, for example, are measured such that the ratio of the inclusion area to diamond area can be calculated. In this way, the size of the inclusion is calibrated relative to the size of each diamond so they can be compared between diamonds.

In vision analysis software for a preferred embodiment of the invention, particular known dimensions of the gem (e.g., from precise laboratory measurement of diameter, which can have a precision to the thousandths of a mm) are used so that the number of pixels per actual unit of length can be calculated for each gem image. This allows the dataset derived from images to be compatible with the dataset derived from non image measurements, such as laboratory or operator measurements. For example, in the event an existing data base structure (database objects and data fields) is in the form of actual length or actual size, the calibration of pixels per length dimension permits a conversion of pixel data (such as number of pixels) into actual length and actual area form, or vice versa. Also, preferably, an operator may interactively measure face-up proportions of the gem, such as table size, pavilion/lower halve ratio, and star length ratio.

Figure 3:
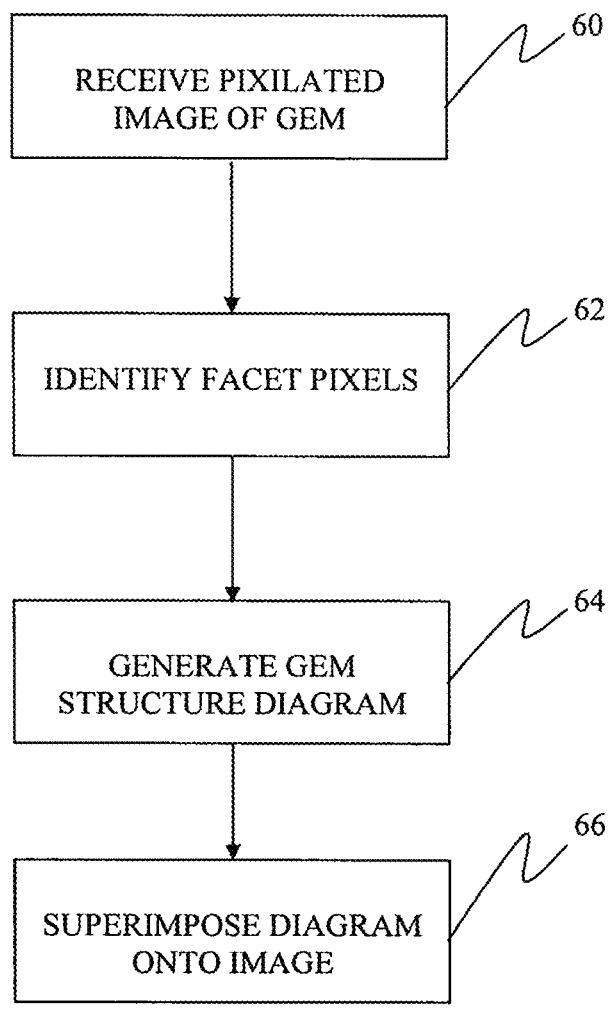
FIG. 3 is a flow diagram illustrating the generation of a gem diagram according to an embodiment of the invention.
Figure 5A:
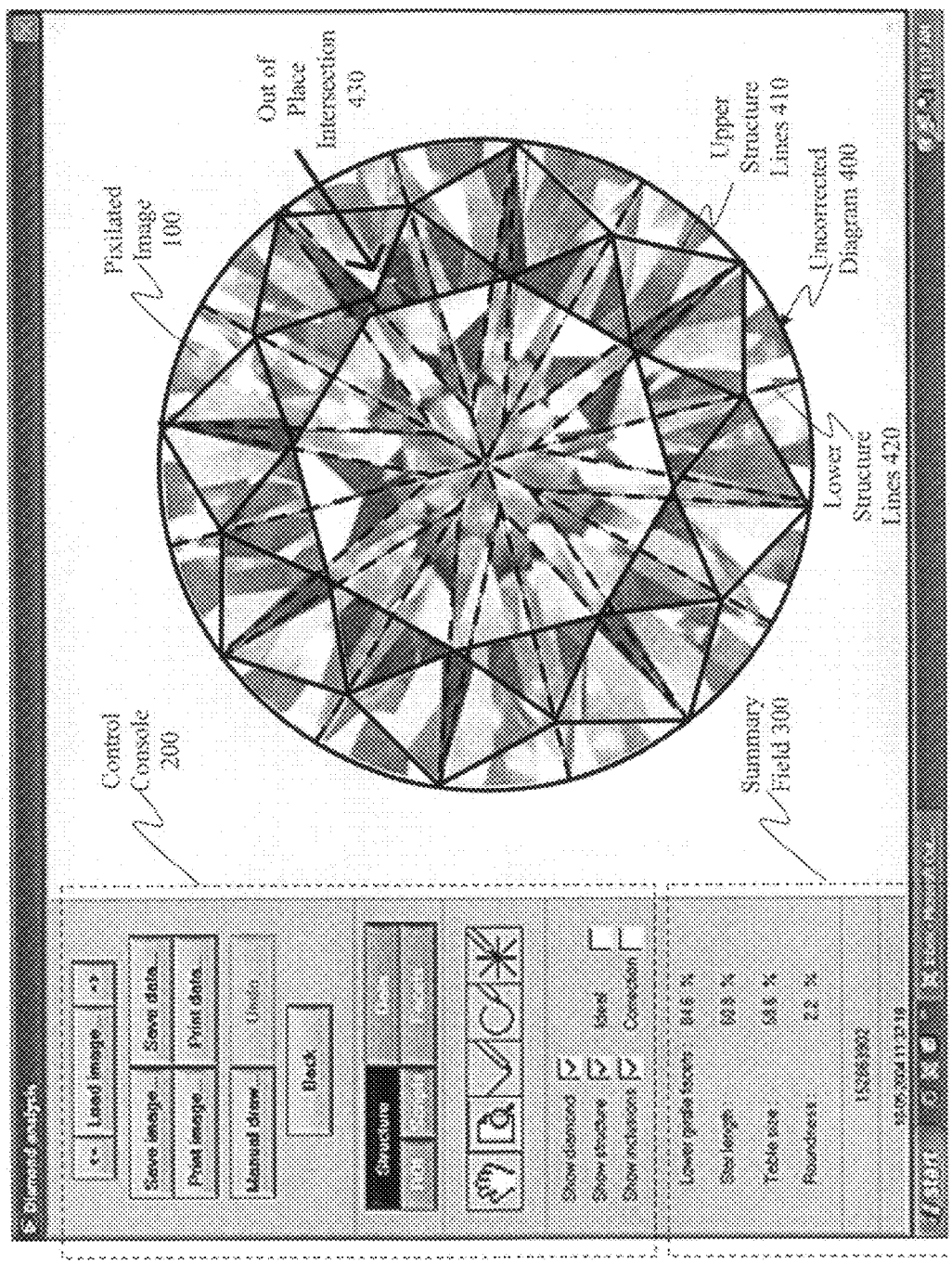
FIG. 5A is an exemplary illustration of an uncorrected gem diagram according to an embodiment of the invention.

Returning now to the generation of a gem structure diagram in operation 64 of FIG. 3, several other features were implemented in connection with the development of that operation. For example, a correction sub-program was developed in order to complete diagrams with missing edges and/or correct out of place intersections. FIG. 5A provides an exemplary illustration of an uncorrected gem diagram 400 superimposed onto a gem image 100, as may be output as an initial gem structure diagram in operation 64 of FIG. 3. In the screen shot, it can be seen that the generated uncorrected structure diagram 400 has an out-of-place intersection 430. Preferably, the lower structure lines 420 of the diagram 400 are rendered to be readily distinguishable from the upper structure lines 410, for example, by using various color combinations and/or solid and dashed line combinations. Also visible is control console 200 and summary field 300, as shown, by which features of the underlying program are selected. Control console 200 may be configured to permit, in addition to the "structure" function, selection of a "data" function, of an "ROI" function, a "scripts" function, a "facets" function, and a "manual draw" function, among others.

Figure 5B:
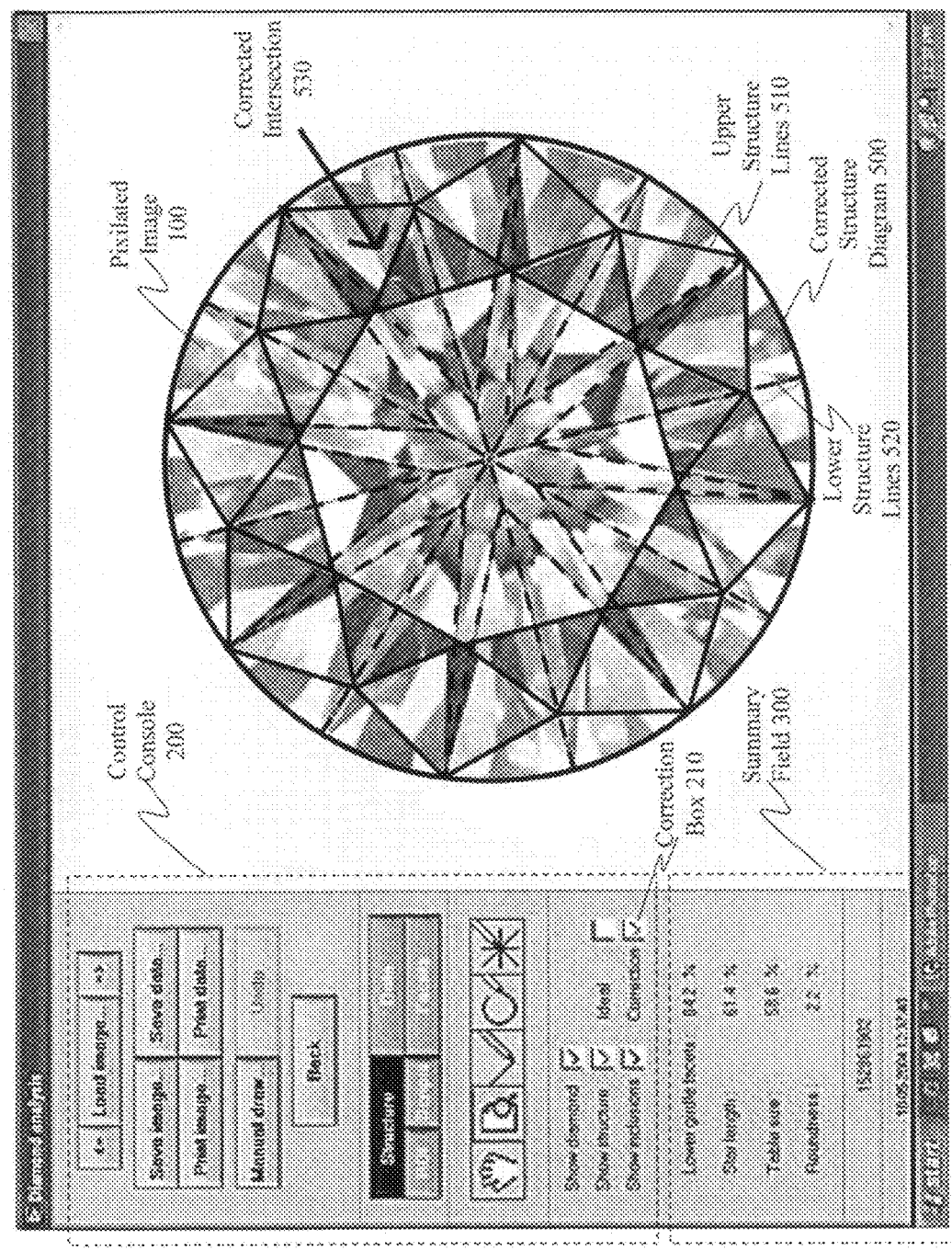
FIG. 5B is an exemplary illustration of a corrected gem diagram according to an embodiment of the invention.

In FIG. 5B, an exemplary illustration of a corrected structure diagram according to an embodiment of the invention is provided. Within this embodiment, a user selects correction box 210 to cause a corrected diagram 500 to be displayed. As can be seen in FIG. 5B, corrected diagram 500 includes corrected intersection 530. The correction of the intersection is achieved by a comparison between the modeled edges and the facet edges detected by the Vision analysis software. In one embodiment of the vision analysis software, edge detection analysis starts with the outline of the gem, and works its way to the center of the gem using sweeps of conventional edge detection software tools. The correction function preferably performs additional sweeps from inside to outside, using the already found facet junctions as references.

Figure 5C:
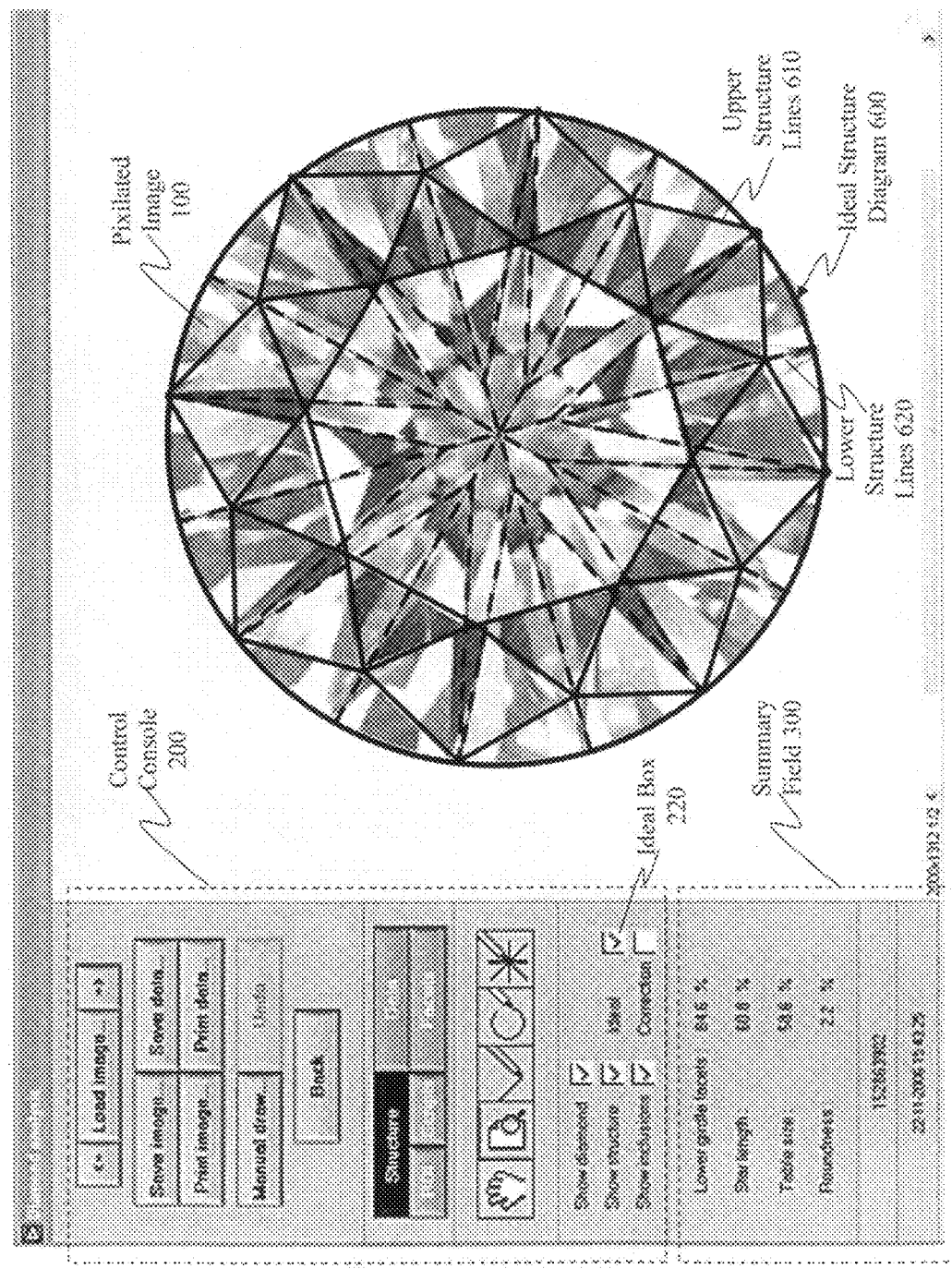
FIG. 5C is an exemplary illustration of a diagram of an ideal structure for a gem according to an embodiment of the invention.

FIG. 5C, illustrates another feature implemented in connection with the generation of a gem structure diagram which may be provided according to an embodiment of the invention—the generation of an "ideal" symmetry gem diagram. Within this embodiment, a user selects the box 220, labeled "Ideal," in order to generate a diagram based upon the actual structure diagram obtained for the gem, for example diagram 400 of FIG. 5A, but which is further extrapolated to have perfect symmetry. This is illustrated as ideal structure diagram 600 in FIG. 5C. A comparison of the alignment of the lines of ideal structure diagram 600 with the facet edges in the pixilated image 100 reveals a number of locations where there are various degrees of misalignment. Therefore, the combined image permits the user to more easily identify where the structure of the actual gem departs from one that has perfectly symmetry.

Figure 5D:
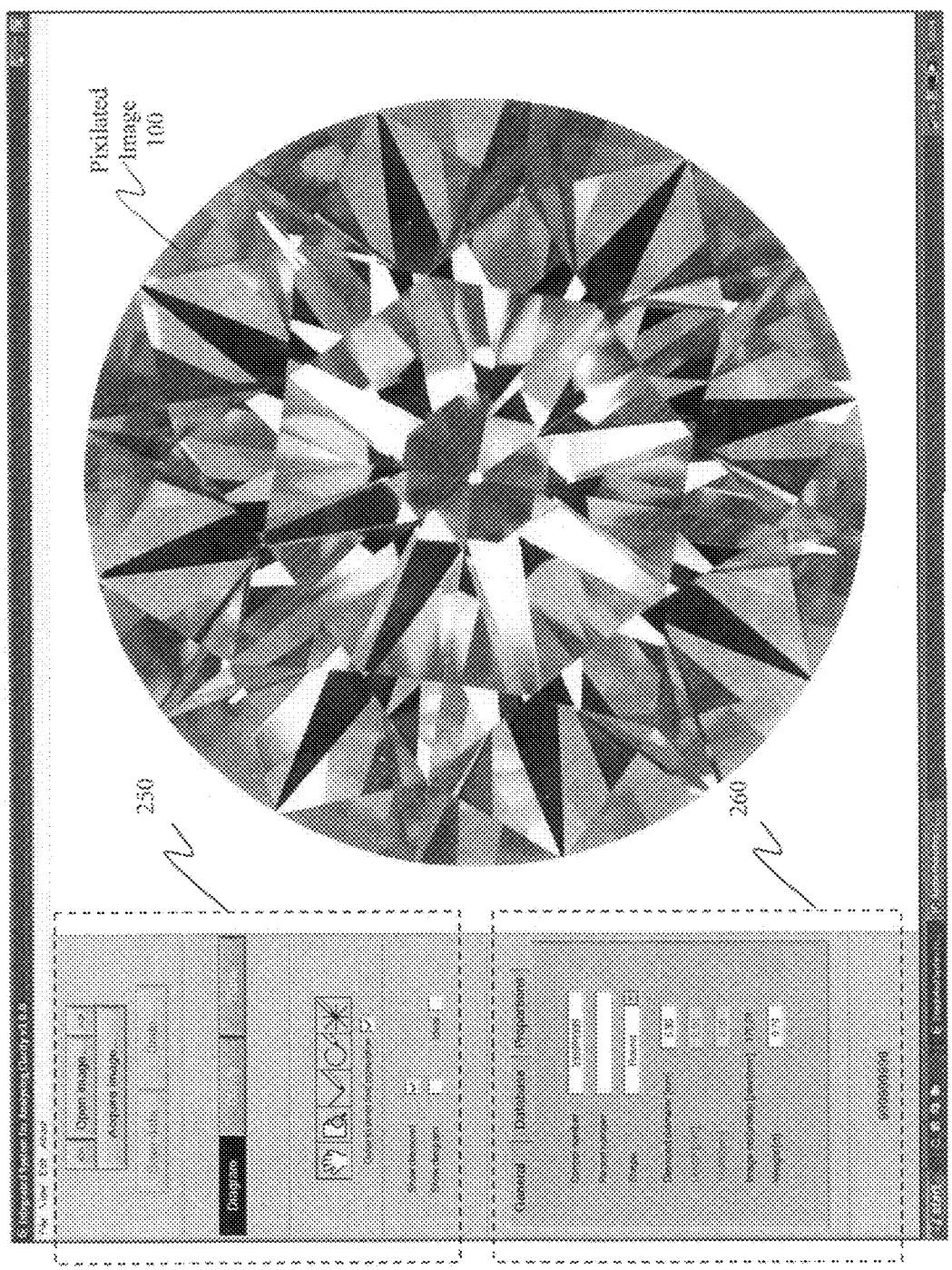
FIG. 5D is an exemplary illustration of a screen shot of an alternative screen configuration displaying a pixilated image of a gem according to another embodiment of the invention.

FIG. 5D provides an exemplary screen shot of an alternative screen configuration displaying and processing a pixilated image of a gem according to another embodiment of the invention. Illustrated on the left side of the screen shot are various controls. Control console 250 permits the user to select between acquiring a new image, or opening an existing one. Also, controls for saving data and canceling an operation are provided. Other buttons in control console 250 permit the user to select between "Diagram"—which involves creation of a gem structure diagram, "Clarity"—which involves clarity analysis, or "Data"—which involves access to a database and data entry for the gem being processed. Gem information group 260 provides a data entry interface and data displays of information relating to the gem being processed in connection with the database. In gem information group 260, it can be seen that several tabs—"General", "Database" and "Proportions"—are provided for different information about the gem. The information that may be accessible through the "General" is illustrated in FIG. 5D. For example, for the gem having control number 999999999, the diameter—5.90 [mm], the shape—round, the image calibration for the image—170.28 [pixels/mm], and the weight—0.70 [cts], of the gem are shown in FIG. 5D. The "Database" tab may provide access to other information to or from the database about the gem being processed. The "Proportions" tab may provide access to information about the cut proportions of the gem being processed. It is to be understood that pre-existing data from the database may be displayed, or new data obtained for the gem being processed may be entered, by way of the gem information group 260.

Returning to FIG. 1, once a gem structure diagram is generated and superimposed onto the pixilated image in operation 12, clarity characteristics of the gem may then be mapped as a function of the gem structure diagram. Operations 14 and 16 represent several of the operations undertaken as a part of such mapping in accordance with an embodiment of the invention.

In the designated region of interest operation 14, an operator identifies a small region of the pixilated image where an inclusion of interest is located. Further image analysis is then performed on the identified region. In particular, a region of interest (ROI) tool may be provided by which an operator can draw a ROI boundary around a grade setting inclusion to designate a subset of the pixilated image data for analysis and to exclude extraneous data. The ROI may take the form of a two-dimensional box defined by two points which is chosen by the operator and which contains the grade setting inclusion.

Working with a ROI, instead of the whole image, also allows the image analysis to run much faster because there are far less pixels to process compared to the entire image of the gem. In particular, use of the ROI tool greatly simplifies the process of extracting inclusions from an entire diamond image, for example, which typically takes the form of a mottled background full of bright reflections.

Following the designation of an ROI in operation 14, operation 16 is preferably undertaken to isolate inclusions within the ROI. This involves running several vision analysis scripts in order to identify pixels representing the inclusions within the ROI, and displaying the results for review by the operator. In a preferred embodiment, the vision analysis scripts are composed of a series of vision analysis algorithms or filters. These algorithms/filters may then form a string of tasks that can be run on an original digital image. When applied to the original image, the goal of the script is to isolate the grade setting inclusion from its surrounding region of interest. Preferably, the combinations of algorithms/filters used in the scripts are selected for their effectiveness in detecting the types of inclusions which are typically encountered in clarity grading. Once isolated, the pixels that represent the inclusion can be measured and analyzed in a later stage.

Figure 7A:
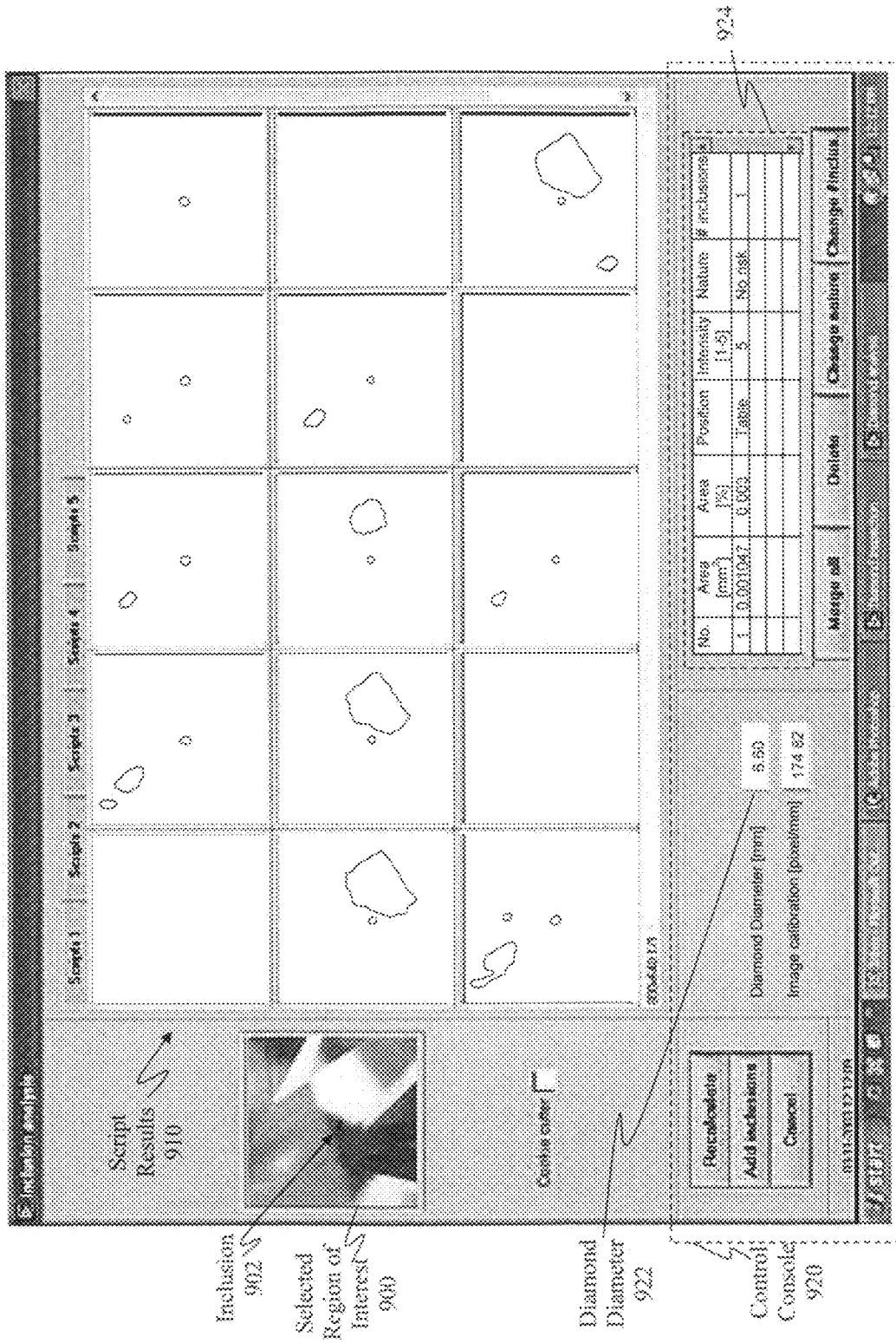
FIG. 7A is an exemplary illustration of an example of a screen shot displaying returned script results according to an embodiment of the invention.

FIG. 7A provides an example of a screen shot of the inclusion analysis screens that may be provided in an embodiment of the invention. The selected region of interest 900 is displayed on the left side of the screen. Inclusion 902 is visible within this image. In FIG. 7A, script results 910 are exemplary illustrations of the results of running the various scripts according to an embodiment of the invention. The operator may then select the result of one of the scripts and save the result, select a result and then edit it to best fit the inclusions, or simply trace the feature manually if no result is acceptable. In FIG. 7A, it can be seen that of the scripts shown, the script in upper right-hand corner appears to provide the best fit to the inclusion 902 that appears in selected region of interest 900. It is noted that several of the script result panes in FIG. 7A are blank. This may be because, for example, for the particular script the specified thresholds were not met, or some other condition required by the particular script for detection of an inclusion was not present in the pixel data for region of interest 900. It is also to be noted that in addition to the script results that are visible in FIG. 7A, additional scripts may be run and the script results presented to the operator by way of tabbed sets of results. In FIG. 7A the tabs labeled "Scripts 2", "Scripts 3", "Scripts 4", and "Scripts 5" represent additional sets of script results. It is also to be understood that the number of vision analysis scripts that are actually run depends upon how well the scripts perform in isolating inclusions that typically are encountered. Poorly performing scripts may be eliminated so as to present the operator only with results from the best performing scripts. Once a suitable isolation of the inclusion is obtained, further calculations on the inclusions 902 in the selected region of interest 900 are conducted.

A number of different scripts containing combinations of filters such as brightness thresholds, hole filling routines, particle size filters, and edge detection filters among others have been developed in connection with the present invention. Specific implementations of these individual types of filters are available as built-in features of the IMAQ Vision Builder software from National Instruments. In formulating scripts used in the present invention, a number of these filtering techniques are applied in succession to obtain the desired result. Once a particular combination of filters is determined, the specific implementations of the selected filters can be selected in the IMAQ Vision Builder software, and then integrated into the LabView software from National Instruments. An example of a combination and sequence of selected ones of these filters which can function as a script in accordance with the present invention is:

1) "Extract Color Planes"—flatten image from 3 color bands to 1 black and white;
2) "Lookup Table: Square"—Apply square stretch to image;
3) "Threshold: Manual"—Choose pre-selected thresholds, for example, only include 165 to 255;
4) "Particle Filter"—filter out clusters of pixels not between 5 to 50,000;
5) "Advanced Morphology Label Objects"—identify each non-contiguous object;
6) "Advanced Morphology Remove Borders"—remove object touching the edge of the ROI.

Another script example is:
1) Extract Color Planes: HSI—Intensity (flatten color image into grayscale)
2) Look—up Table: Square
3) Image Mask: from ROI (region of interest)
4) Threshold: Manual Threshold
5) Advanced Morphology: Separate Objects
6) Particle Filter
7) Advanced Morphology: Label Objects
8) Advanced Morphology: Remove borders A further script example is:
1. Extract Color Planes: HSI—Intensity (flatten color image into grayscale)
2. Look—up Table: Square
3. Image Mask: from ROI (region of interest)
4. Threshold: Automatic Threshold
5. Advanced Morphology: Fill Holes
6. Advanced Morphology: Separate Objects
7. Particle Filter
8. Advanced Morphology: Label Objects
9. Advanced Morphology: Remove borders At first, 80 scripts were developed and organized into 5 different tabulated pages of script results, each containing 15 batches of script results per page. A test was then conducted using about 80 selected images for the purpose of reducing the number of scripts to a more practical number. The testing focused on the performance of each individual script ranked in terms of how broadly applicable each was to the batch of images under test. Each script was also judged relative to the cumulative performance of the most broadly applicable scripts. In other words, consideration was given to how many additional inclusions were successfully captured that were not already covered by highest ranking scripts. This procedure insured that the performance of the vision analysis application continued to improve as more scripts were added. A performance key was assigned to each script and based on this performance key a ranking was made to determine what scripts performed best. The ranking allows the best performing scripts to be placed on the first page and the worst to be deleted. The number of scripts was eventually reduced to 3 sets of 15 scripts.

The software that is used to outline facet edges and create diagrams of the diamonds may also help improve the performance of the clarity analyzing scripts. Because some inclusions are difficult to separate from bright reflections at facet junctions, the diagram produced by this software can be used to isolate the inclusions from the reflective facets. This function can either be turned on manually or automatically because appending pieces of inclusion is a relatively quick and easy process.

Figure 7B:
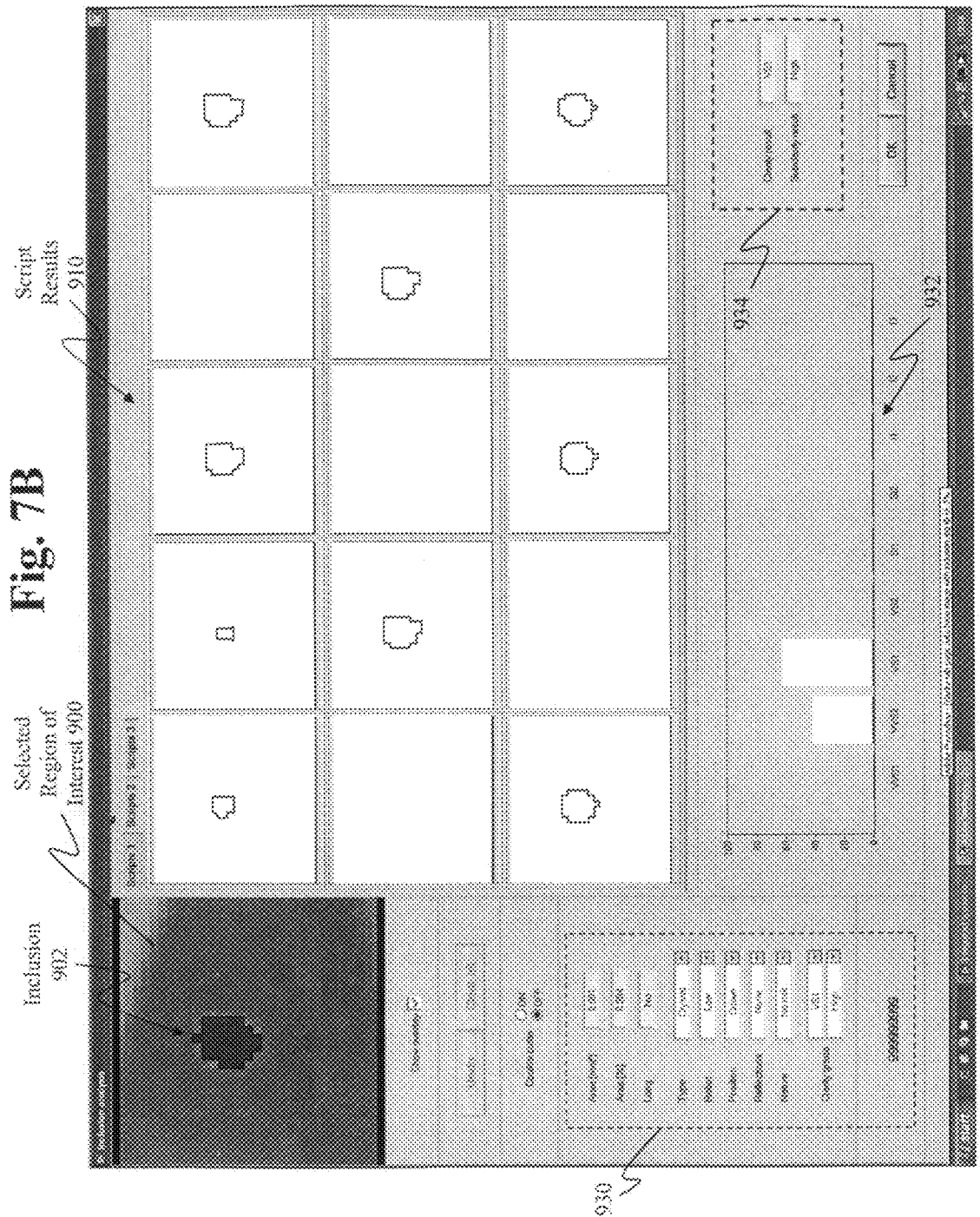
FIG. 7B is an exemplary illustration of an example of a screen shot displaying returned script results using a different screen layout according to another embodiment of the invention.

FIG. 7B provides an example of a screen shot of a different configuration of an inclusion analysis screen for displaying returned script results according to another embodiment of the invention. As with the embodiment of FIG. 7A, the selected area of interest 900 and inclusion 902 of interest are displayed in the left side of the screen. Exemplary script results 910 are illustrated for "Scripts 1" of three possible groups of scripts ("Scripts 1," "Scripts 2," and "Scripts 3"), as indicated by the labeled tabs. For the example shown, the differences between the displayed script results 910 and the inclusion of interest 902 may result in the operator electing to view script results for Scripts 2 and/or Scripts 3, or, alternatively, to manually edit or trace the overlay of the inclusion to provide a better fit.

On the lower left side of the screen shot of FIG. 7B, grouping 930 provides information entry points and/or calculation results for the inclusion 902 of interest. Along the bottom of the screen a bar graph is provided in chart 932 indicating the relative distance between the center of two adjacent clarity grades, for possible clarity grades of VVS1, VVS2, VS1, VS2, SI1, SI2, I1, I2, and I3. In the bottom right hand corner of the screen, the results of the clarity analysis are displayed in section 934. The "clarity result" refers to the clarity grade category in which the particular gem has been assigned, and the "subclarity result" refers to the position of the particular gem within the range which makes up the assigned "clarity result."

In other embodiments, the facet outlines may be merged with a graphical representation of the inclusion from the scripts to produce a plot similar to what is currently done manually by some graders. It has been noted that although the area of the inclusion will be necessary for calculating a clarity grade, only the outline needs to be plotted for internal inclusions and a break line needs to be plotted for surface reaching inclusions.

Returning to FIG. 1, once the inclusion is suitably isolated, operation 18 determines characteristics of the isolated inclusion from the pixels corresponding to the isolated inclusion. Although any of several inclusion characteristics may influence the ultimate clarity grade of a gem, a few characteristics have been identified to be particularly influential. Namely, the size, position, relief, number, and "type" of a gem's inclusions have been identified. Accordingly, a brief description of each is provided below, along with a discussion of their respective significance. Further, as determined by the methods and systems described herein, the numerical and other relationships for inclusions and other clarity characteristics of a gem can be used to predict the influence of the inclusions or other clarity characteristic upon the clarity grade for the gem. Co-pending U.S. patent application Ser. No. 12/287,187, now issued as U.S. Pat. No. 8,402,066 filed even date herewith, entitled "A Method And System For Providing A Clarity Grade For A Gem," and incorporated herein by reference in its entirety, describes an approach which breaks down clarity grades into separate yet interacting inclusion parameters in order to predict a clarity grade based upon a set of inclusions parameters for a particular gem which may be obtained as described herein.

The size of an inclusion has the strongest overall impact on the clarity grade and the larger the inclusion, the greater the impact. The size of an inclusion is represented in the face up view of a diamond as a two dimensional object. The length and width of a two dimensional inclusion may be measured directly with a microscope equipped with a measuring graticule. An equation of an ellipse, for example, may then be fed these measurements and used to approximate the inclusion area. A certain degree of error is associated with this approximation which is higher for irregularly shaped inclusions, but with a sufficient quantity of data, errors can be smoothed out to produce general relationships that can be used to predict the influence of the face-up area of an inclusion on the clarity grade. This elliptical approximation of inclusion area has been validated with similar results when using the digital imaging approach described herein, that uses a more precise method which digitizes the outline of the inclusion, counts the number of pixels inside the outline, and then converts the number of pixels into an inclusion size area or area relative to the size of the diamond. The digital imaging approach for determining the size of an inclusion described herein is utilized in the preferred embodiment of the invention.

An important aspect of the inclusion size parameter analysis is the conversion of the area of the inclusion to a ratio of the inclusion area to the size of the diamond. Experienced diamond graders have been consulted and confirm that the size of the diamond is considered in the decision making process. Although most graders would agree that similarly sized inclusions should not equally impact a 1.0 ct stone versus a 10.0 ct stone, diamond graders cannot explain or predict, in a hypothetical sense, how the size of the diamond will influence the results. They must first see an example and visually compare the inclusion size to the size of the diamond in order to confidently provide a clarity grade.

The positioning of an inclusion can also influence the final clarity grade of a gem. In the face up view of a diamond, for example, a grader may view and classify one of two inclusions differently even if both inclusions are of similar relative sizes depending on their position parameter. There are two main explanations for this. First, there is a tendency for an inclusion to be more visible when it is located towards the center of the diamond (and thus also closer to the center of an observer's attention) as opposed to a location closer to the girdle. A second explanation is that a more explicit facet distribution and facet reflection pattern toward the edge of most diamonds may tend to hide inclusions, and reduce their visibility, making them less important.

The "relief" of an inclusion is a categorical measure of the contrast between the inclusion and the surrounding facet distribution and reflection pattern of a diamond. As a general rule, the brighter an inclusion is, the more visible an inclusion appears to be to the grader who may lower the clarity grade as a result.

Many times one clarity characteristic will determine the clarity grade of a diamond while other clarity characteristics in the stone will have no significant impact on the final clarity grade call. The most severe clarity characteristic in a diamond is called the grade setting inclusion. The presence of multiple clarity characteristics of equal severity to the grade setting inclusion can lower the clarity grade further. Face-up reflections of inclusions or mirror images can look like additional inclusions to an observer and are therefore graded the same as additional inclusions. Depending on the location of an inclusion in a diamond, the distribution of facets can cause the inclusion to appear multiple times or be reflected, especially when the inclusion is positioned deep and near the culet of the diamond. Generally, the number of inclusions has been found to have a minor role, but a sufficient quantity of additional inclusions of similar size or reflections of inclusions can typically lower the clarity grade by a half a grade.

Clarity characteristics, classified according to their "type" have typically been divided into two categories: internal and surface reaching inclusions. Each of these categories may be further subdivided according to particular clarity grading procedures, into a number of subdivisions of "type" characteristics, some common and others uncommon. However, since many of the uncommon subdivisions such as chips, bruises, etc. are not believed to differ fundamentally from the more common clarity characteristics such as crystals or feathers, the uncommon categories may be lumped with the common ones.

With the foregoing in mind, operation 18 (FIG. 1) and the determination of characteristics of the inclusion which has been isolated in operation 16, will now be discussed in greater detail. Characteristics of the inclusions are determined by utilizing the pixels identified in operations 14 and 16 as representing the inclusion.

The inclusion size parameter can be calculated by the summing of all the pixels within the inclusion area that are isolated by a script. Then a calculation can be made to find the inclusion area size relative to the size of the diamond area (the calculation of which is based on the diameter). Preferably, a pixel-to-pixel calculation is made for this determination of the relative size of the inclusion. In the control console 920 illustrated in FIG. 7A, the operator may enter diameter data into the diameter data field 922. As explained above, this diameter data is preferably from precise laboratory measurement of the diameter of the gem, which can have a precision to the thousandths of a mm. This permits calculations in both pixel and length units to be made from the pixilated image data. From this information, calculations may be performed which provide an image calibration (in pixels per mm), total gem and inclusion areas (in mm$^2$), and relative area. Preferably, the inclusion size or surface area (in pixels) and the diamond areas (in pixels) are measured first, and the digital images are calibrated using the input of the diamond diameter. With this information a calculation of inclusion size relative to the diamond size, and other size parameters, can be made. For example, the ratio of the inclusion size area (in pixels) to the total area of the diamond (in pixels), and inclusion area [mm], can be calculated. An example of the results of such calculations can be seen in FIG. 7A in table 924. For the example provided in FIG. 7A it can be seen that the entered diamond diameter [mm] is 6.60, the image calibration result [pixels per mm] is 174.82, the area [mm$^2$] is 0.001047, and the area [%] is 0.003.

In the example of FIG. 7B, in grouping 930, the inclusion being analyzed has been determined to have an area of 0.001 [mm$^2$], to have a relative area of 0.004 [%], to not have a "long" shape, to be a "crystal" type, to have a "relief" which is "low," to be positioned in the crown, to have no reflections, and to have been previously evaluated as a having a clarity of "VS1" and "High." In the embodiment illustrated in FIG. 7B, the results appearing in the box labeled 934 are automatically generated by the application. These results are then automatically copied in the box in the left lower corner of grouping 930 for data base purposes. This entry can be changed by the operator.

Also as part of operation 18 of FIG. 1, other relevant pixel-related inclusion parameters such as location mapping of the inclusion, and relief, can be determined or computed in a semi-automated way from the isolated inclusion and gem image pixel information.

Figure 6A:
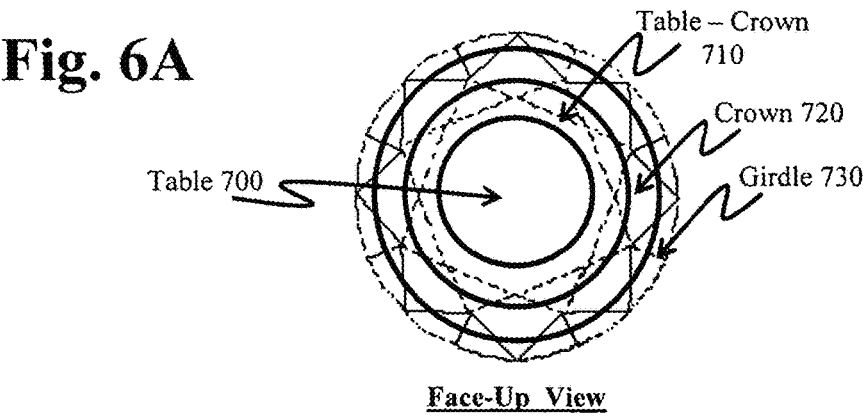
FIG. 6A is an exemplary top view illustration of a gem identifying inclusion location identifier regions according to an embodiment of the invention.
Figure 6B:
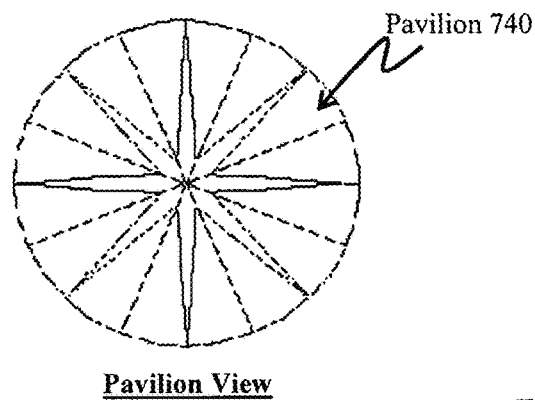
FIG. 6B is an exemplary illustration of a gem identifying a pavilion region of the inclusion location identifier regions according to an embodiment of the invention.
Figure 6C:
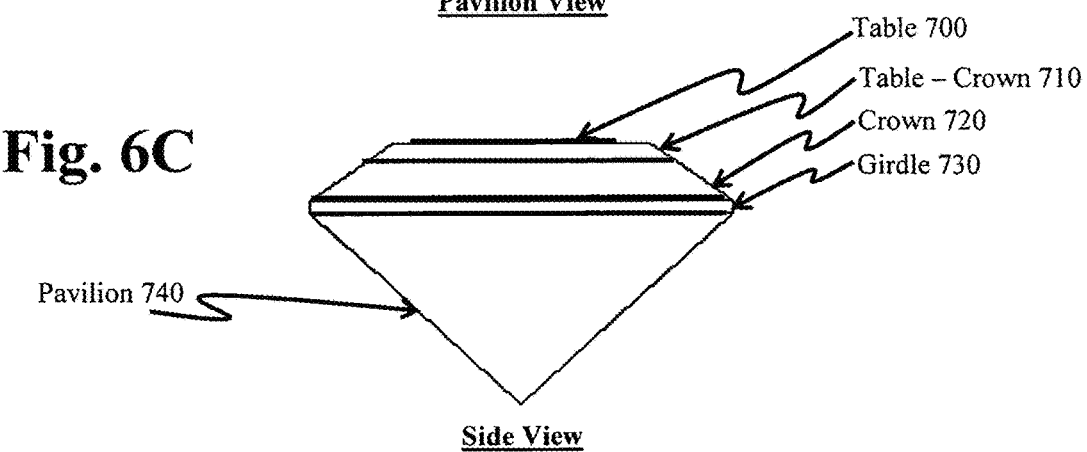
FIG. 6C is an exemplary side view illustration of a gem inclusion location identifier regions according to an embodiment of the invention.

In connection with a location mapping operation, position identification guidelines were developed by which the positions (locations) of inclusions or other clarity characteristics can be described, collected and analyzed in a consistent way. In a preferred embodiment, five inclusion location identifier regions are employed: (1) "Table," (2) "Table-Crown," (3) "Crown," (4) "Girdle," and (5) "Pavilion." FIGS. 6A-6C, provide examples of the regions of a diamond structure that correspond to these inclusion location identifier regions. The first four identifiers effectively divide the face-up area of a diamond into four concentric rings, as illustrated in FIG. 6A. These rings are defined from the center outward. In FIGS. 6A and 6C, Table 700 references the "Table" region, which is centered in the table of the diamond and encompasses an area of about 80% of the total area of the table. Table— Crown 710 references the "Table—Crown" transition region, which extends from the boundary of the "Table" region out to approximately 50% of the star facets. Crown 720 references the "Crown" region, which extends from the boundary of the "Table-Crown" region to about one-third of the upper girdle half. Girdle 730 references the "Girdle" region, which extends from the boundary of the "Crown" region to the remainder of the girdle of the diamond. Finally, as illustrated in FIGS. 6B and 6C, Pavilion 740 references the "Pavilion" region, which corresponds to all of the pavilion side of the diamond. The foregoing inclusion location identifier regions can be correlated to the pixilated image and gem structure diagrams for a gem of interest. The inclusions, once isolated by operations 14 and 16, can then be sorted into locations defined by these inclusion location identifier regions: table, table-crown, crown girdle, or pavilion. The precise location of an inclusion is preferably determined by the digital gravity point of the inclusion's pixels—the average of all pixel locations.

To determine an inclusion's relief parameter, a pixel histogram of the inclusion may be measured relative to the histogram of the surrounding ROI selection. The relief of the inclusion is then determined by matching the relationship between the two histograms to one of a set of reference images with known relief factors. Alternatively, the relief of an inclusion may be calculated from the pixilated image data by using the ratio of the average pixel value within the inclusion to the average pixel value of an area of the image with a constant radius surrounding the inclusion.

As for the number of inclusions, although an automatic correction factor for reflections may be implemented, the total number of inclusions may also be entered manually. The type of an inclusion may be entered manually as well.

Returning to FIG. 1, once the characteristics of the isolated inclusion have been determined in operation 18, operations 14-18 may be repeated for other inclusions within the currently designated region of interest, block 20. When all of the inclusions within a region of interest have been characterized, it is determined in block 22 whether there are more regions of interest to be processed. If so, operations 14-20 are repeated until all regions of interest have been processed. In operation 24, the characteristics which have been determined for the inclusions of interest are then used to determine a clarity grade for the gem. For example, a clarity grade may be determined for the gem based upon the relative areas of the inclusions, the relief of the inclusions, the location of the inclusions, the "type" of the inclusions and/or the number of inclusions in the gem. The above referenced co-pending patent application Ser. No. 12/287, 187, now issued as U.S. Pat. No. 8,402,066 entitled "A Method And System For Providing A Clarity Grade For A Gem," describes methodologies and a system for parameterizing the inclusion and gem characteristics provided by the system and method of the present invention, and accounting for the interrelationships of the parameterized inclusion properties to provide a clarity grade result.

Figure 8:
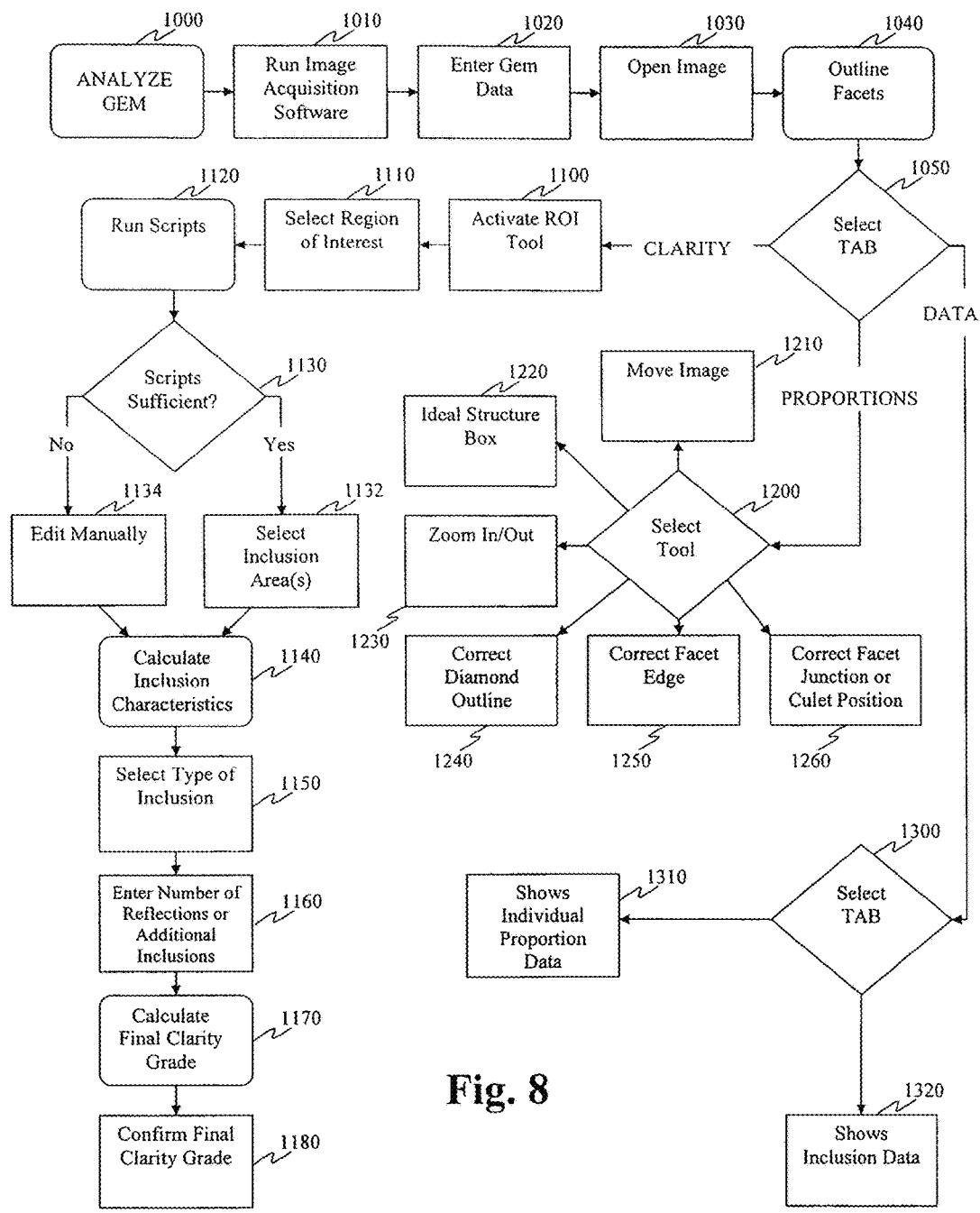
FIG. 8 is a high level flow chart illustrating various functionalities provided by an embodiment of the invention.

FIG. 8 shows a high level flow chart illustrating various functionalities provided by an embodiment of the invention. Within such embodiment, the procedure for analyzing a gem 1000 includes running image acquisition software at step 1010. Gem data is then entered at step 1020, which may include the gem's dimensions (e.g., diameter, weight, etc.) and/or control number. Next, a pixilated image file of the gem, obtained by the imaging software in step 1010, is opened at step 1030. Then the facet edges of the gem may be outlined in step 1040. Alternatively, following step 1030, a modified step 1040 may be processed in which less than a full gem structure diagram is obtained, for example data sufficient to for image calibration (FIGS. 7A, 7B), and/or for correlating the position identifier regions 710-740 (FIG. 6C) to the pixilated image.

Once step 1040 has been completed, an operator may select any of three tab selections at step 1050. The selections available in step 1050 are: CLARITY, DATA, or PROPORTIONS.

The CLARITY tab is selected to obtain a clarity grade. Such procedure begins, for example, with activating the region of interest tool at step 1100 and selecting a particular region of interest at step 1110. A plurality of scripts for isolating inclusions within the region of interest are then run at 1120. At step 1130, the operator is permitted to determine whether any of the scripts are sufficient to satisfactorily isolate the inclusions. If sufficient, the best performing script is selected at step 1132, otherwise the inclusion is manually outlined by the operator at step 1134. The pixel-related inclusion characteristics (e.g., size, relief, and position) are then calculated and/or determined by the procedure at step 1140. The operator enters inclusion type at step 1150 and the number of reflections or additional inclusions at step 1160. Then, a clarity grade is calculated at step 1170 (e.g., by using a look-up table or algorithm) and confirmed by the operator at step 1180.

The PROPORTIONS tab is selected in step 1050 in order to make adjustments to the gem structure diagrams obtained from step 1040. This step may be undertaken prior to selecting the CLARITY tab in order to verify that the gem structure diagrams acceptably depict the outlines of the gem's facets. Upon selecting the PROPORTIONS tab, the operator is presented with a number of choices in step 1200. The operator may, for example, move the acquired image of the gem at step 1210 within the view; select the ideal symmetry structure box at step 1220 to cause a gem structure diagram to be generated having ideal symmetry; zoom the gem image in/out at step 1230; correct the diamond outline (gem structure diagram) at step 1240; correct the facet edges in the gem structure diagram at step 1250; or correct the facet junction or culet position in the gem structure diagram at step 1260.

Should the operator desire to obtain particular data pertaining to the gem, the DATA tab would be selected at step 1050, in order to proceed to step 1300. By way of step 1300, the operator may either obtain pixel-related inclusion data (e.g., size, relief, or position) at step 1320, or individual proportion data (e.g., star lengths, upper half lengths, table size, etc.) at step 1310.

As is apparent from the foregoing description of embodiments of the present invention, the various disclosed methods, operations or systems may be implemented in a conventional desktop or laptop computer coupled to a digital imaging device which is positioned to obtain images of a gem supported and illuminated in an illumination apparatus such as described herein. Further, many of the functionalities of the present invention provided for clarity measurements may be embodied in the form of executable computer code or instructions stored in a computer-readable medium, such as a hard-disc, CDROM, DVD, memory card, USB memory module, semiconductor memory, and the like.

The present invention has been described above with reference to several different embodiments. However, those skilled in the art will recognize that changes and modifications may be made in the above described embodiments without departing from the scope and spirit of the invention. Furthermore, while the present invention has been described in connection with a specific processing flow, those skilled in the art will recognize that a large amount of variation in configuring the processing tasks and in sequencing the processing tasks may be directed to accomplishing substantially the same functions as are described herein. These and other changes and modifications which are obvious to those skilled in the art in view of what has been described herein are intended to be included within the scope of the present invention.

What is claimed is:

1. A method for determining clarity of a gem comprising:
at a computer with a processor and memory,
receiving a pixilated image of the gem including facets in the gem;
mapping, using the pixilated image of the gem, the facets of the gem;
correcting the mapped facets of the gem using a vision detection algorithm;
receiving, at least one region of interest, the region of interest including pixels within the pixilated image of the gem;
for each received region of interest,
isolating the pixels within the region of interest within the gem;
running a plurality of scripts on the isolated pixels within the region of interest;
identifying, using the plurality of scripts, any inclusions or inclusion reflections, within the pixels in the region of interest,
wherein the plurality of scripts are ranked according to a performance key;
counting a number of identified inclusions within the area of interest;
determining an area of the identified inclusions within the area of interest;
determining a location for each of the identified inclusions within the area of interest;
determining a relief for each of the identified inclusions within the area of interest; and
determining a clarity grade for the gem, based on the area, location, and relief of the identified inclusions and inclusion reflections within the regions of interest in the gem.

2. The method of claim 1 wherein the plurality of scripts include at least one of the following filters: brightness thresholds, hole filling routines, particle size filters, and edge detection filters.

3. The method of claim 1 further comprising, by the computer, generating a modeled outline of the gem, based on the pixilated image.

4. The method of claim 3 further comprising, by the computer, measuring the gem using both an actual image and the modeled outline.

5. The method of claim 4 wherein measuring includes measuring a dimension of the gem.

6. The method of claim 4 wherein measuring includes measuring an area of the identified inclusions.

7. The method of claim 4 wherein measuring includes measuring a position of the identified inclusions.

8. The method of claim 1 wherein the determining the clarity grade for the gem includes determining a ratio between a size of the gem and the area of the identified inclusion or inclusion reflections.

9. The method of claim 1 wherein the determining the clarity grade for the gem includes calibrated pixel data, from the pixelated image of the gem.

10. A non-transitory computer-readable medium-storing instructions which, when executed by a processor, cause the processor to perform operations:
receiving a pixilated image of the gem including facets in the gem;
mapping, using the pixilated image of the gem, the facets of the gem;
correcting the mapped facets of the gem using a vision detection algorithm;
receiving, at least one region of interest, the region of interest including pixels within the pixilated image of the gem;
for each received region of interest,
isolating the pixels within the region of interest within the gem;
running a plurality of scripts on the isolated pixels within the region of interest;
identifying, using the plurality of scripts, any inclusions or inclusion reflections, within the pixels in the region of interest,
wherein the plurality of scripts are ranked according to a performance key;
determining a relief for each of the identified inclusions within the area of interest;
providing a user interface for viewing the identified inclusions, for each of the plurality of scripts; and
determining a clarity grade for the gem, based on the area, location, and relief of the identified inclusions and inclusion reflections within the regions of interest in the gem.

11. The non-transitory computer-readable medium of claim 10 wherein the plurality of scripts include at least one of the following filters: brightness thresholds, hole filling routines, particle size filters, and edge detection filters.

12. The non-transitory computer-readable medium of claim 10 further comprising, by the computer, generating a modeled outline of the gem, based on the pixilated image.

13. The non-transitory computer-readable medium of claim 12 further comprising, by the computer, measuring the gem using both an actual image and the modeled outline.

14. The non-transitory computer-readable medium of claim 13 wherein measuring includes measuring a dimension of the gem.

15. The non-transitory computer-readable medium of claim 13 wherein measuring includes measuring an area of the identified inclusions and inclusion reflections.

16. The non-transitory computer-readable medium of claim 13 wherein measuring includes measuring a position of the identified inclusions.

17. A system configured to determine clarity of a gem comprising:
a computer with a processor and memory, the computer configured to, receive a pixilated image of the gem including facets in the gem;

map, using the pixilated image of the gem, the facets of the gem;

correct the mapped facets of the gem using a vision detection algorithm;

determine at least one region of interest, the region of interest including pixels within the pixilated image of the gem;

for each received region of interest, isolate the pixels within the region of interest within the gem;

run a plurality of scripts on the isolated pixels within the region of interest;

identify, using the plurality of scripts, any inclusions or inclusion reflections, within the pixels in the region of interest, wherein the plurality of scripts are ranked according to a performance key;

determine an area of the identified inclusions within the area of interest;

determine a relief for each of the identified inclusions and inclusion reflections within the area of interest; and determine a clarity grade for the gem, based on the area, location, and relief of the identified inclusions within the regions of interest in the gem.

18. The system of claim 17 wherein the determine the clarity grade for the gem includes to determine a ratio between a size of the gem and the area of the identified inclusion.

19. The system of claim 17 wherein the determine the clarity grade for the gem includes calibrated pixel data, from the pixelated image of the gem.

20. The system of claim 10 wherein the plurality of scripts include at least one of the following filters: brightness thresholds, hole filling routines, particle size filters, and edge detection filters.

21. The method of claim 1 wherein the receiving at least one region of interest, is by a user input.

22. The non-transitory computer-readable medium of claim 10 wherein the receiving, at least one region of interest, is by a user input.

* * * * *